Jan. 14, 1941. G. C. LODGE Plant Pat. 440

FUCHSIA

Filed Feb. 7, 1940

INVENTOR.
GEORGE C. LODGE.

BY Oberlin, Limbach & Day
ATTORNEYS.

Patented Jan. 14, 1941

Plant Pat. 440

UNITED STATES PATENT OFFICE

440

FUCHSIA

George C. Lodge, Painesville, Ohio, assignor to The Cole Nursery Company, Painesville, Ohio, a corporation of Ohio Application February 7, 1940, Serial No. 317,735

1 Claim. (Cl. 47—60)

Figures 1, 2:
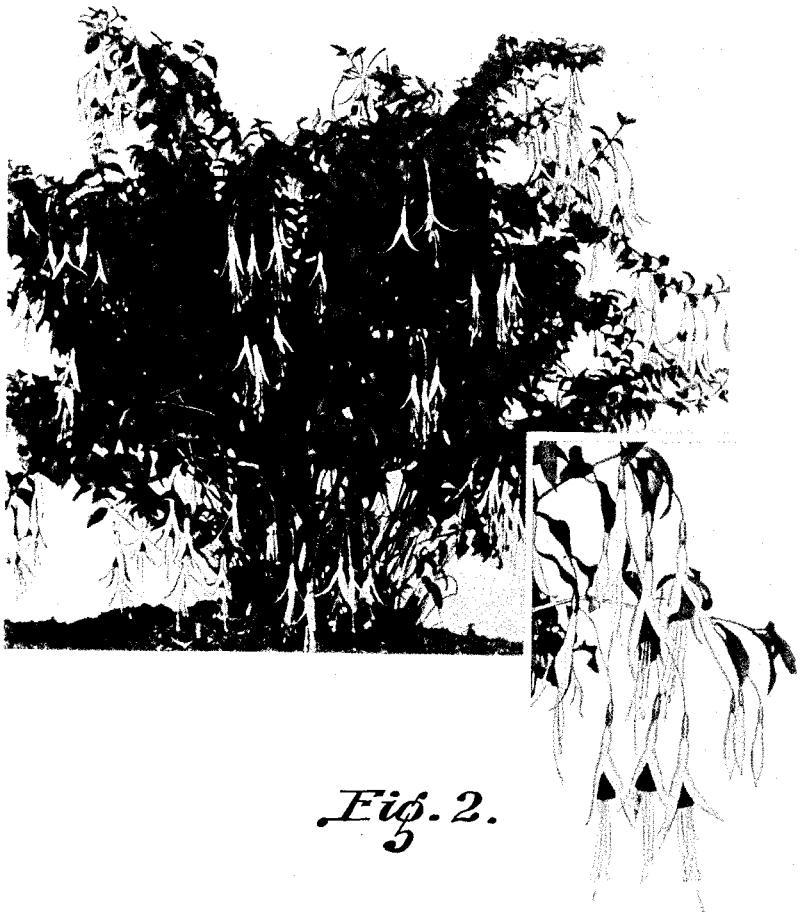

This invention relates, as indicated, to a new and improved fuchsia and more particularly to a plant of this genus (family Onagraceae) which has proven hardy in the latitude of northern Ohio and has other desirable attributes.

Fuchsias are a genus of decorative shrubs native to tropical America and long popular in the North as a greenhouse plant. Because of their showy flowers and graceful form they would make an ideal plant both for the herbaceous border and more formal planting but for their usual tenderness. It was, therefore, a primary purpose of the present inventor to originate a new fuchsia of improved color and form and which would grow as a hardy perennial without winter protection in a climate at least as severe as that of northern Ohio.

Success was obtained with a seedling of *Fuchsia magellanica* variety riccartoni originated in the vicinity of Painesville, Ohio, after a great many seedlings tested during many years had failed to survive the rigours of winter.

This new plant is an herbaceous shrub which freezes to the ground each winter, coming up in the spring from eyes formed below the ground level. It may therefore, to all intents and purposes, be treated as a hardy perennial. Established plants in northern Ohio attain a height of about two feet by the third week in June at which time the blooming season begins, and eventually reach a height of about three feet by the end of the growing season.

Established plants of three or more years of age show from twenty to forty stems from the ground, some of which attain a caliper of from ½ inch to ¾ inch at ground level. From the third week in June until late fall or early winter the blossoms continue and increase until the plant is cut down by severe frosts. The resistance to frost is approximately equal to that of the hardy chrysanthemums so that the early light frosts are weathered without appreciable injury.

The bush is of strong, upright habit with graceful, somewhat pendulous branches and branchlets densely massed which at the height of the blooming season carry a great many blossoms hanging singly on slender peduncles from the axils of the leaves.

The foliage is of a deep glossy green appearance which adds greatly to the attractiveness of the plant and forms an admirable background for the blossoms.

The accompanying illustration shows (Fig. 1) a typical plant of my new variety of *Fuchsia magellanica* variety riccartoni, much reduced, in full color and (Fig. 2) a branch tip bearing blossoms in various stages of opening on a somewhat larger scale.

A detailed description of this new variety of fuchsia follows:

Calyx:
- *Color.*—Rose Red (Ridgway Pl. 12).
- *Length.*—1⅓ to 1½″.
- *Width.*—1 to 1½″.

Sepals: 4.

Corolla:
- *Color.*—Mulberry Purple at first (Ridgway Pl. 11), changing to Aster Purple (Ridgway Pl. 12).

Stamens: Rose Red (Ridgway Pl. 12).

Anthers: Rose Red (Ridgway Pl. 12).

Styles: Rose Red (Ridgway Pl. 12).

Stigmas: Rose Red (Ridgway Pl. 12).

Corolla:
- *Length.*—½ to ¾″.
- *Width.*—¼ to ⅜″.

Stigma:
- *Length.*—About $\frac{1}{16}$″, slightly longer than wide.

Style and Pistil:
- *Length.*—2 to 2½″.

Anthers: Usually 8, length about $\frac{3}{32}$ to ⅛″, flat $\frac{1}{16}$ by $\frac{1}{32}$″.

Stamens: Usually 8.

Length of flower from end of peduncle to stigma: 2¼ to 2¾″.

Peduncle:
- *Length.*—1 to 2″.

Bud:
- *Length.*—1 to 1½″.

Leaves:
- *Length.*—Generally 1 to 2″, width generally ½ to 1″ ovate-lanceolate to lanceolate, irregularly serrate, opposite or whorled in threes.

Petiole:
- *Length.*—¼ to ½″.

Stem: Pomegranate Purple to Bordeaux (Ridgway Pl. 12).

Stems and leaves: Glabrous.

Note: These descriptions are based upon mature development produced on good soil with slight acid reaction in Lake County, Ohio.

The plant is easily reproduced asexually, as by cuttings. While it is realized that the characteristics of the plant of this invention may perhaps alter slightly due to unusual environment and the like, the characteristics of such plant as described, and particularly its hardiness, clearly differentiate the same from all previously known varieties.

I therefore point out and distinctly claim as my invention and discovery:

The new variety of *Fuchsia magellanica* variety riccartoni herein described and illustrated, of vigorous and upright growth, extremely floriferous, and particularly characterized by its hardiness.

GEORGE C. LODGE.